US009063052B2

(12) United States Patent
Folgeroe et al.

(10) Patent No.: US 9,063,052 B2
(45) Date of Patent: Jun. 23, 2015

(54) INLINE MEASURING APPARATUS AND METHOD

(75) Inventors: Kjetil Folgeroe, Hjellestad (NO); Jan Kocbach, Bergen (NO)

(73) Assignee: TECOM AS, Bergen (NO)

( * ) Notice: Subject to any disclaimer, the term of this patent is extended or adjusted under 35 U.S.C. 154(b) by 267 days.

(21) Appl. No.: 13/641,735

(22) PCT Filed: Apr. 19, 2011

(86) PCT No.: PCT/NO2011/000134
§ 371 (c)(1),
(2), (4) Date: Oct. 17, 2012

(87) PCT Pub. No.: WO2011/133046
PCT Pub. Date: Oct. 27, 2011

(65) Prior Publication Data
US 2013/0033272 A1 Feb. 7, 2013

(30) Foreign Application Priority Data

Apr. 19, 2010 (NO) .................................. 20100560

(51) Int. Cl.
*G01N 22/00* (2006.01)
*G01N 33/28* (2006.01)

(52) U.S. Cl.
CPC ............. *G01N 22/00* (2013.01); *G01N 33/28* (2013.01)

(58) Field of Classification Search
CPC ............................... G01N 33/38; G01N 22/00
See application file for complete search history.

(56) References Cited

U.S. PATENT DOCUMENTS

| 5,223,796 | A | | 6/1993 | Waldman |
| 5,926,024 | A | * | 7/1999 | Blount et al. ................. 324/324 |
| 6,335,959 | B1 | * | 1/2002 | Lynch et al. .................. 73/61.44 |
| 8,027,794 | B2 | * | 9/2011 | Xie ................................. 702/50 |

(Continued)

FOREIGN PATENT DOCUMENTS

WO 0046545 A1 8/2000

OTHER PUBLICATIONS

Written Opinion for counterpart application PCT/NO2011/000134, mailed Oct. 19, 2012 (12 pages).

(Continued)

*Primary Examiner* — Jermele M Hollington
(74) *Attorney, Agent, or Firm* — Abelman, Frayne & Schwab

(57) ABSTRACT

An inline measuring apparatus (10) is operable to measure hydrate, wax, break-through of formation water and/or scale (150) on an inside surface of a wall (100) of a pipe (40) for guiding fluid. The apparatus (10) includes an electronics unit (30) coupled to a sensor arrangement (20) disposed in a spatial extensive manner into the wall (100) of the pipe (40) for sensing the growth (150). The electronics unit (30) in cooperation with the sensor arrangement (20) is operable to perform a series of dielectric measurements at a plurality of interrogating frequencies for determining a nature and spatial extent of the growth (150). The sensor arrangement (20) includes a plurality of sensors have mutually different sensing characteristics in relation to their spatial sensing region and/or their sensitivity to different fluid components present in operation within the pipe (40). Optionally, the apparatus (10) is capable of being operated synergistically in a plurality of different operating modes which enables detection of thin film formation at an inside wall of the pipe (40) as well as a measurement of bulk properties of fluid present within the pipe (40).

27 Claims, 12 Drawing Sheets

(56) References Cited

U.S. PATENT DOCUMENTS

| | | |
|---|---|---|
| 2003/0011386 A1* | 1/2003 | Xie et al. ............... 324/694 |
| 2007/0224692 A1 | 9/2007 | Agar |
| 2009/0204346 A1 | 8/2009 | Xie |
| 2009/0223284 A1* | 9/2009 | Buhring ............... 73/40.5 A |
| 2011/0214511 A1* | 9/2011 | Fjerdingstad ........... 73/861.41 |

OTHER PUBLICATIONS

Thorvald Jakobsen & Kjetil Folgero, "Dielectric Measurements of Gas Hydrate Formation in Water-in-Oil Emulsions Using Open-Ended Coaxial Probes," Meas. Sci. Technol. 8 (1997) 1006-1015 Apr. 1997.

International Preliminary Report on Patentability for counterpart application PCT/NO2011/000134, mailed Sep. 24, 2012 (59 pages).

* cited by examiner

INLINE MEASURING APPARATUS AND METHOD

FIELD OF THE INVENTION

The present invention relates to inline measuring apparatus for detecting hydrate formation and for assuring flow, for example to apparatus for sensing hydrate formation within pipes, namely close to walls of the pipes, which could potentially obstruct flow. Moreover, the present invention concerns methods of detecting hydrate formation and assuring flow. Furthermore, the present invention also concerns software recorded on data storage media, wherein the software is executable on computing hardware for use when implementing these methods. Additionally, the invention relates to apparatus and associated methods of detecting growth of wax and/or scale and/or break-through of formation water.

BACKGROUND OF THE INVENTION

Problems related to crystallization and/or deposition of wax, hydrate and scale during production and transportation of hydrocarbons are potentially capable of causing considerable economic losses to petroleum industries. Moreover, break-through of formation water can also create problems. These losses arise through the cost of chemicals, reduced production, equipment failure, and so on. Flow assurance is thus becoming an increasing challenge as depth and step-out distances to new oil and gas fields are increasing in order to exploit more marginal fossil fuel reserves.

Gas hydrates are ice-like structures which form when water molecules assemble themselves into a 'cage' around a small organic molecule, for example around molecules present in oil and natural gas. Hydrates exhibit complex behaviour which represents a problem, given a large number of micro- and macro-scale phenomena involved in the process of hydrate formation, such as nucleation, crystal growth, agglomeration, break-up, entrainment and deposition along pipelines in transient multiphase flow conditions. Two distinct processes are observed in pipelines. A first process occurs at a pipeline wall with the formation of a hydrate layer (coat) as the pipeline wall is a coldest point in a system including the pipeline, providing an excellent nucleation and growth site. A second process is the formation and transport of hydrate particles in a bulk of a flow.

Current methods of preventing formation of hydrate, wax and scale may include various approaches, and combinations including:

(i) applying chemicals, for example using hydrate inhibitors such as methanol, glycol and/or new polymers injected at an upstream end of a pipeline, and wax inhibitors;
(ii) applying mechanical devices to remove or dislodge deposits, for example pigging of the pipeline;
(iii) by applying temperature changes, for example by circulating hot fluid, by applying electrical heating to the pipeline, and by applying insulation to the pipeline and an associated subsea Xmas-tree; and
(iv) by lowering an operating pressure to the pipeline, if feasible, at a constant temperature.

Hydrate inhibitor injection is today a main method of preventing formation of hydrate in transport pipelines during operation of an oil and/or gas field.

A most common way to monitor gas hydrate formation in pipelines involves using non-localized methods utilizing pVT (p=pressure, V=volume, T=temperature) measurements. In the pVT-methods, a phenomenon that gas hydrates can only form within a special pressure and temperature region (namely a "stability zone") is exploited in order to monitor the pipeline. Gas hydrate inhibitors are injected based upon:

(a) the calculated/measured hydrate stability zone;
(b) worst case scenarios for pressure and temperature conditions;
(c) water occurrence; and
(d) loss of the inhibitor to any non-aqueous phases present.

In many cases, high safety margins are used to account for uncertainties associated with measuring the above factors, as limited localized monitoring solutions are available along the pipeline; in other words, measurements indicative of, for example, hydrate formation are only available at periodic spatial intervals along the pipeline. This results in a high consumption of an inhibitor liquid, frequent pigging to avoid blocking of pipelines, in addition to the environmental challenges associated with such operations. Due to a high inhibitor dosage requirement, a significant increase in capital expenditure and operational expenditure can arise, in particular at high water cut conditions. Also, despite all these efforts, hydrates do form that can have considerable economic and safety impacts. Thus, systems for early warning and detection of hydrate formation are therefore of considerable value to industry. Moreover, early detection of one or more break-throughs of formation water is also important in industry, on account of production of formation water potentially resulting in sudden increases in water cut and thereby increased risk of hydrate formation arising.

Some localized methods of monitoring hydrate formation along pipelines have been suggested. In a published US patent application no. 2007/0276169, a method of measuring a degree of inhibition of hydrate formation in a fluid is described, namely to determine a susceptibility to gas hydrate formation in the fluid. In the same patent application (see also a published scientific paper Tohidi 2009: Tohidi, Bahman, Antonin Chapoy, and Jinhai Yang. 2009; "Developing a Hydrate-Monitoring System", SPE Projects Facilities & Construction 4, no. 1 (3). doi:10.2118/125130-PA, http://www.onepetro.org/mslib/servlet/onepetropreview?id=SPE-125130-PA&soc=SPE) a measurement of the dielectric constant for water history has also been suggested as a method of early warning of hydrate formation. A published US patent application no. 2007/0224692 describes an electromagnetically-based method of measuring water and hydrate content in a production fluid. The method is based upon measuring a complex permittivity in the fluid at two or more frequencies. This method is based on bulk measurements, and is not applicable to detecting very thin hydrate coatings at an inner wall of a pipe.

Principles for on-line detecting and monitoring of formation of gas hydrates in pipelines using permittivity measurements for plural frequencies were first suggested and published in the year 1996 by Jakobsen and Folgerø, wherein Kjetil Folgerø is one of the inventors of the present invention:

Jakobsen 1996: Jakobsen, T. "Clathrate hydrates studied by means of time-domain dielectric spectroscopy," Dr. Scient. Thesis, University of Bergen, 1996. ISBN 82-7406-016-4;

Folgerø 1996: Folgerø, Kjetil. "Coaxial sensors for broadband complex permittivity measurements of petroleum fluids," Dr. Scient. Thesis, University of Bergen, 1996. ISBN 82-994032-1-9; and thereafter Jakobsen 1997: Jakobsen, T., and K. Folgerø. "Dielectric measurements of gas hydrate formation in water-in-oil emulsions using open-ended coaxial probes". Measurement Science and Technology 8, no. 9 (1997): 1006-1015.

In these publications, it was shown that hydrate formation close to a wall of a sample cell could be monitored using permittivity measurements performing by employing an open-ended coaxial probe. A Norwegian patent no. 312169 describes use of a similar permittivity sensor to monitor water fraction in thin liquid layers. However, such a sensor topology applies a point measurement, namely it is only sensitive to fluid properties in a small spatial region around the probe. This spatially localized sensitivity is a drawback, on account of a single point measurement giving a measurement volume which is so limited such that it may not be representative for an actual hydrate deposition. This limitation is possible to overcome by using a significant number of spatially-distributed point measurement sensors. However, such an approach would be costly to implement on account of each of these sensors requiring a separate corresponding electronics unit in order to measure at all points simultaneously. Moreover, the measurement precision of an open-ended coaxial probe is limited, and cannot be controlled independently of the probe's sensitivity depth and frequency operation range.

A published US patent application no. 2008/0041163 describes a method of detecting particles in a fluid; the method involves passing an ultrasonic signal through the fluid. This method is applicable for identifying gas hydrate nucleation, but it is however not suitable for detecting thin hydrate coatings.

A published U.S. Pat. No. 5,756,898 describes an acoustic method of measuring an effective internal diameter of a pipe containing flowing fluids. The patent application describes a manner in which this method can be applied for measuring hydrate layer thickness or scale/wax deposition. Moreover, a published U.S. Pat. No. 6,470,749 describes another method of measuring a build-up of deposits on an inner surface of a pipeline containing flowing fluid, this method using pulsed ultrasonic Doppler measurements. Further acoustic methods for measuring deposit build-up on insides of pipe walls involve using a guided acoustic wave sensor as described in U.S. Pat. No. 6,568,271, and a similar principle is described in a published U.S. Pat. No. 6,513,385. However, these acoustic methods do not provide a required sensitivity for detecting very thin layers of coating for the case of non-uniform layers with varying bonding between pipe and layer; thus, detection of thin non-uniform coatings associated with hydrate formation is not possible using acoustic methods for providing warnings. Moreover, a depth sensitivity of apparatus and associated measurement techniques in these patents is difficult to control, thereby potentially resulting in unreliable measurements being achieved in practice.

Possible techniques for measuring break-through of formation water include measuring the amount and salinity of water present. A sudden increase in water-content and water-salinity indicates break-through of formation water. The salinity of water can be estimated from the water conductivity, and there exist several apparatuses for measuring water conductivity in water-continuous mixtures. There is, however, a need for more accurate methods to measure the conductivity for oil-continuous mixtures.

SUMMARY OF THE INVENTION

The present invention seeks to provide an inline measuring apparatus for detecting hydrate formation and for assuring flow, for example for sensing hydrate formation within pipes, namely close to walls of the pipes. Moreover, the present invention seeks to provide an inline measuring apparatus for detecting scale and/or wax deposition and/or break-through of formation water.

According to a first aspect of the present invention, there is provided an inline measuring apparatus as claimed in appended claim 1: there is provided an inline measuring apparatus for measuring at least one of hydrate, wax, break-through of formation water and scale presence on or close to an inside surface of a wall of a pipe for guiding fluid in operation, characterized in that the apparatus includes an electronics unit coupled to a sensor arrangement disposed in a spatially extensive manner into the wall of the pipe for sensing at least one of the hydrate, wax, break-through of formation water and scale presence; and the electronics unit in cooperation with the sensor arrangement is operable to perform a series of dielectric measurements at a plurality of interrogating frequencies for determining a nature and spatial extent of at least one of the hydrate, wax scale, break-through of formation water, an amount of formation water.

The invention is of advantage in that it provides a more reliable approach for determining a degree and extent of at least one a hydrate, a wax, scale, a break-through of formation water and an amount of formation water by coupling interrogating radiation efficiently into spatial regions of the pipe whereat such hydrate, wax and/or scale is likely to form in operation and in which formation water will reside after breakthrough of formation water having occurred.

A term "close to" as used above is optionally to be construed to mean in a spatial region of not more than 20 mm, more preferably not more than 5 mm, and most preferably not more than 1 mm. The sensitivity depth is beneficially adjustable to specific applications for the present invention. Optionally, a boundary of the spatial region is defined, such that measurement sensitivity has reduced to $1/e$ of a maximum measurement sensitivity provided; $e=2.71828$ approximately.

Optionally, the inline measurement apparatus is implemented, so that the sensor arrangement is operable to measure a salinity and a conductivity in a liquid film formed within the spatial measurement region of the sensor arrangement.

Optionally, the inline measuring apparatus is implemented so that the sensor arrangement is disposed in an axial and/or circumferential and/or spiral manner on an inside surface of the wall of the pipe.

Optionally, the inline measuring apparatus is implemented such that the sensor arrangement is disposed in a multisegment path on an inside surface of the wall of the pipe, the multisegment path being constructed to cover an area of the inside surface giving an effective 2-dimensional measurement coverage. In other words, the sensor arrangement is implemented to provide measurement over an extensive area in comparison to point measurements from point probes.

Optionally, the inline measuring apparatus is implemented such that the sensor arrangement is wrapped around the pipe in a spiral manner. Such a sensor arrangement is pertinent, for example, where the pipe is fabricated from a dielectric material, for example PEEK or ceramic materials, enabling the sensor arrangement to be potentially implemented without coming into direct contact with an inner wall surface of the pipe.

Optionally, the inline measuring apparatus is implemented so that the sensor arrangement includes at least a transmission line. More optionally, the transmission line is implemented as a leaky cable, a coplanar waveguide, a leaky waveguide, a microstrip line, and/or a slotline. Beneficially, the waveguide, cable and/or transmission line have associated therewith a spatial sensing region which is localized to within a few millimetres (mm) of, namely is "close to" as aforementioned, a spatial extent of the waveguide, cable and/or transmission line.

Beneficially, the sensor arrangement includes a plurality of sensors have mutually different sensing characteristics in relation to their spatial sensing region and/or their sensitivity to different fluid components present in operation within the pipe. Optionally, the apparatus is capable of being operated synergistically in a plurality of different operating modes which enables detection of thin film formation at an inside wall of the pipe as well as a measurement of bulk properties of fluid present within the pipe.

Optionally, the inline measuring apparatus is implemented such that the sensor arrangement includes a plurality of sensors having mutually different sensing properties. Such mutually different sensing properties makes it possible to measure both deposit/film thickness and permittivity.

Optionally, the inline measuring apparatus is implemented such that the sensor arrangement includes one or more sensors whose spatial measurement region is capable of being dynamically controlled in extent, by varying a permittivity of a material included in the one or more sensors. Beneficially, such dynamic control is achieved by modulating a relative permittivity of a dielectric backing portion of the sensor arrangement.

Optionally, the inline measuring apparatus is implemented such that the sensor arrangement is operable to enable capacitive and/or resistive/conductive measurements between electrodes of at least two mutually different sensors, wherein such measurements include bulk permittivity measurements in a first operating mode in addition to other measurements using the same at least two sensors operating at least in a second operating mode.

Optionally, the inline measuring apparatus is implemented such that the electronics unit is operable to perform time domain reflectometry (TDR) for making a permittivity measurement.

Optionally, the inline measuring apparatus is implemented such that the electronics unit is operable to perform a swept or stepped measurement at a plurality of frequencies from the sensor arrangement.

Optionally, the inline measuring apparatus is implemented such that measurables of the apparatus are reflection coefficients and/or transmission coefficients and/or impedance or a combination of these. Optionally, the inline measuring apparatus is implemented so that an interrogating output from the electronics unit is terminated in a matched load at the sensor arrangement. Optionally, the inline measuring apparatus is implemented such that the sensor arrangement includes a 1-port device terminated in a short circuit. Optionally, the inline measuring apparatus is implemented such that the sensor arrangement includes a 1-port device terminated in an open circuit.

Optionally, the inline measuring apparatus is implemented so that the measurements derived from the sensor arrangement are combined with measurements using another type of sensor principle, namely by employing sensors operating in other physical manners. More optionally, the inline measuring apparatus is implemented such that the other sensor principle provides a temperature measurement. More optionally, the inline measuring apparatus is implemented such that the other sensor principle is a capacitive or inductive sensing principle. More optionally, the inline measuring apparatus is implemented such that the other sensor principle provides a bulk measurement of the permittivity; for example, the bulk measurement of permittivity is achieved by utilizing capacitive or resistive/conductive measurements between two of sensors of the sensor arrangement used for performing spatially localized measurements. More optionally, the inline measuring apparatus is implemented such that the other sensor principle is an ultrasound measurement. More optionally, the inline measuring apparatus is implemented such that the other sensor principle is an optical measurement.

Optionally, the inline measuring apparatus is implemented such that the sensor arrangement includes at least one of: a planar transmission line resonator or a dipole transmission line resonator, wherein a hydrate, wax and/or scale content in a measurement volume of the sensor arrangement is determined from a measured resonance frequency and/or a resonance Q-factor of the planar transmission line resonator or the dipole transmission line resonator.

Optionally, the inline measuring apparatus is implemented such that the sensor arrangement includes at least one sensor which is operable to function as a reference sensor which has a material with known material properties throughout its measurement range. Use of such a reference sensor is capable of being employed to compensate for any zero-reference drift inaccuracies arising in the in-line measuring apparatus.

Optionally, the inline measuring apparatus is implemented such that the sensor arrangement includes an interfacing dielectric material in communication with a layer of hydrate, wax and/or scale formed in operation on an inside surface of the wall of the pipe, the dielectric material exhibiting a similar wettability to an inside surface of the wall of the pipe so that the hydrate, wax and/or scale forms in a representative manner on the interfacing dielectric material. More optionally, the inline measuring apparatus is implemented such that the interfacing dielectric material is a ceramic and/or a polymer plastics material.

According to a second aspect of the invention, there is provided a method of measuring hydrate, wax, break-through of formation water and/or scale presence on an inside surface of a wall of a pipe for guiding fluid in operation, characterized in that the method includes:

(a) using an electronics unit of an apparatus coupled to a sensor arrangement disposed in a spatially extensive manner into the wall of the pipe to interrogate the sensor arrangement for sensing formation of a layer of hydrate, wax, break-through of formation water and/or scale; and (b) using the electronics unit operating in cooperation with the sensor arrangement to perform a series of dielectric measurements at a plurality of interrogating frequencies for determining a nature and spatial extent of the layer of hydrate, wax, breakthrough of formation water and/or scale.

Optionally, the method includes:

(c) performing the measurements at a plurality of frequencies using the sensor arrangement including a plurality of sensors exhibiting mutually different spatial measurement characteristics in relation to the layer of hydrate, wax, break-through of formation water and/or scale to create a matrix of measurement values; and (d) solving a series of simultaneous equations in the electronics unit using the values in the matrix to determine a nature and/or extent of the layer of hydrate, wax, break-through of formation water and/or scale.

Optionally, the method is applied to measure the presence and/or amount of formation water within the pipe.

According to a third aspect of the invention, there is provided a software product recorded on a data storage medium, wherein the product is executable on computing hardware for implementing a method pursuant to the second aspect of the invention.

According to a fourth aspect of the invention, there is provided an inline measuring apparatus for measuring the presence and/or amount of formation water on an inside surface of a wall of a pipe for guiding fluid in operation, characterized in that the apparatus includes an electronics unit coupled to a sensor arrangement disposed in a spatially extensive manner into the wall of the pipe for sensing the formation water; and
the electronics unit in cooperation with the sensor arrangement is operable to perform a series of dielectric measurements at a plurality of interrogating frequencies for determining the presence and/or amount of the formation water.

Thus, the present invention concerns an apparatus which employs complex permittivity measurements within a measurement volume close to the pipe wall to detect thin layers on hydrate, scale, break-through of formation water and/or wax deposits. It will be appreciated that features of the invention are susceptible to being combined in various combinations without departing from the scope of the invention.

DESCRIPTION OF THE DIAGRAMS

Embodiments of the present invention will now be described, by way of example only, with reference to the following diagrams wherein:

FIGS. 1A to FIG. 1C are illustrations of an inline measuring instrument, namely "apparatus", for measuring hydrate, wax, break-through of formation water and/or scale formation within a pipeline or pipe, wherein FIG. 1A is a circumferential implementation, FIG. 1B is an axial implementation, and FIG. 1C is a spiral implementation;

Figure 7:
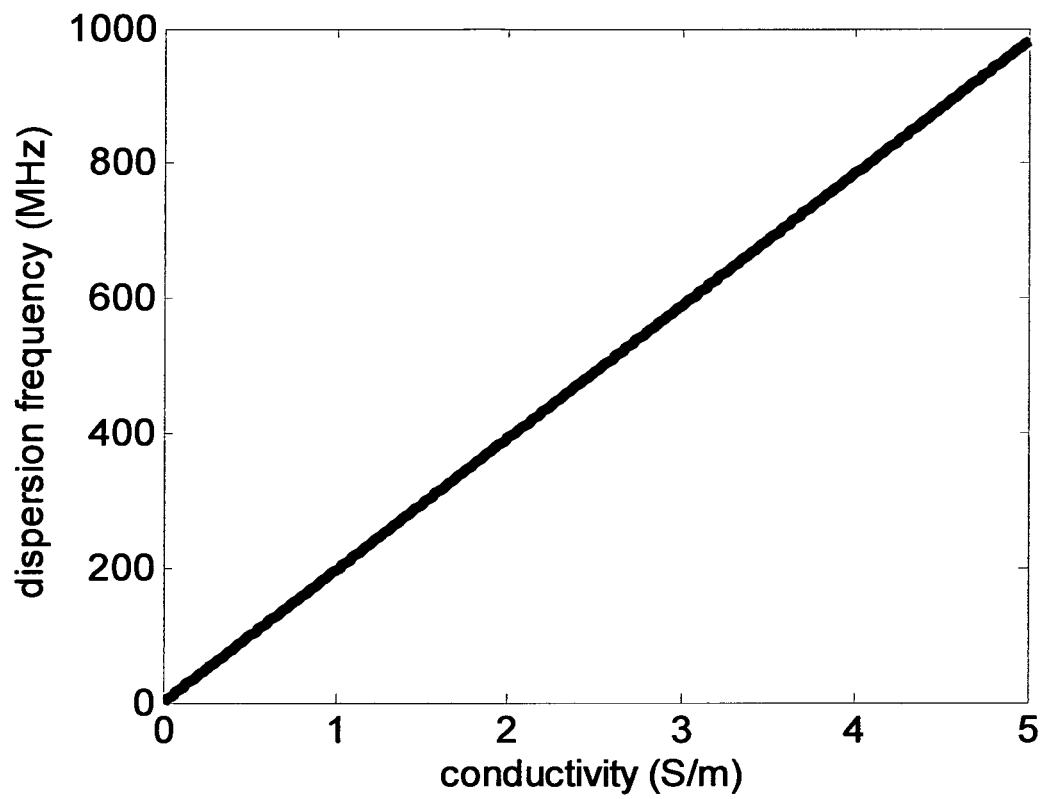
Figure 8:
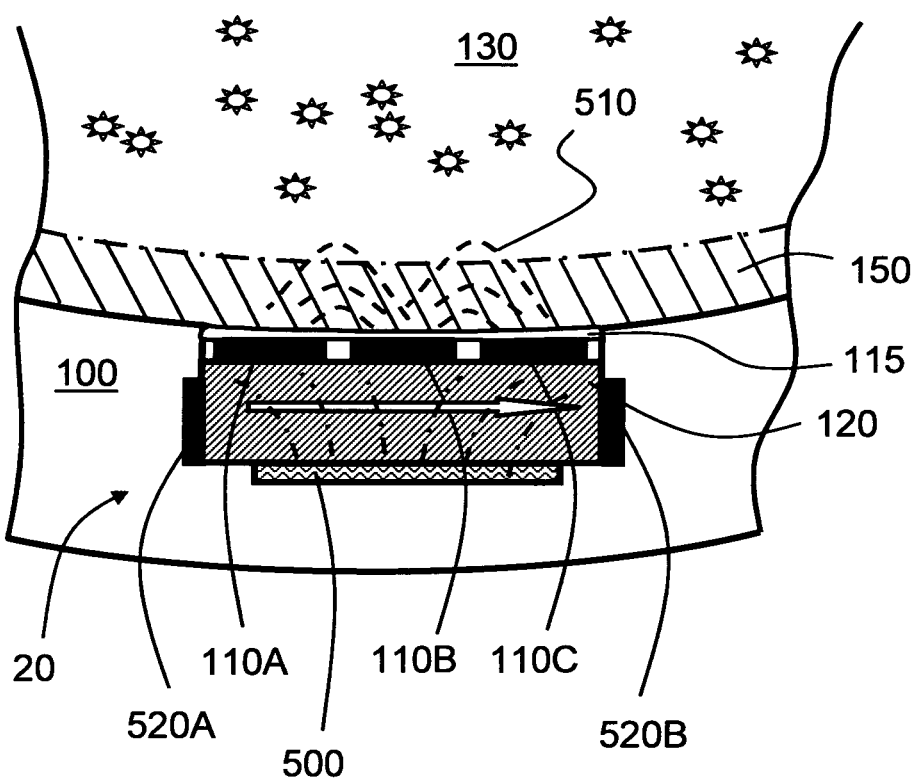

FIG. 7 is a graph of the dispersion frequency of a water-in-oil emulsion as a function of water conductivity for a mixture with 10% water content; and FIG. 8 is an illustration of a sensor arrangement for use in apparatus pursuant to the present invention, wherein the sensor arrangement employs a dynamically adjustable transmission line sensor whose spatial region of measurement is susceptible to being dynamically varied in operation.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS OF THE INVENTION

In overview, the present invention concerns apparatus which utilize complex permittivity measurements within a measurement volume spatially close to a wall of a pipe to detect thin layers of hydrate, scale, and/or wax deposits, and/or amounts of formation water in a liquid film close to a pipe wall. Equipment based on complex permittivity measurements are in use in other fields, for example as described in:
(i) US patent application no. 2009/152624 which pertains to use of a coplanar waveguide for non-invasive measurement on living tissue; and
(ii) U.S. Pat. No. 5,223,796 which pertains to measuring dielectric properties of a material,
but their application to detecting hydrate, wax, break-through of formation water and/or scale deposition is not known.

The present invention relates, for example, to a method and apparatus for measuring deposits of gas hydrates on an inside region of a pipe, and is applicable, for example, for providing early warning of hydrate formation along pipelines. From a viewpoint of known technology, it is perceived in relation to the present invention that there is a need for monitoring solutions for early warning of hydrate formation along pipelines. Known systems for monitoring hydrate formation are not able to detect the very thin layers of hydrates deposited on the pipe wall early in the build-up process with high accuracy. The present invention is thus focused, amongst other things, towards this problem of enhanced measurement accuracy which is not adequately addressed by known measurement systems.

The present invention involves measuring a complex permittivity spectrum in a measurement volume spatially close to a wall of a pipe using an electromagnetic transmission line sensor or a plurality of electromagnetic transmission line sensors, from which a hydrate fraction within the measurement volume is calculated; for a definition of "close", we refer to the foregoing (Summary of the invention). This measurement approach makes it possible to detect very thin coatings of hydrate, for example coatings whose thickness is considerably less than 1 mm, for example a few micrometers thick. Nucleation of hydrates that occurs in the multiphase flow close to wall can also be detected before they stick to the wall. Moreover, this measurement approach is of advantage compared to prior art in that only a region which is a coldest point in a system is considered, namely a point providing a potentially excellent nucleation and growth site for hydrates. Compared with previously proposed techniques using open-ended probes, the present invention uses a line measurement instead of a point measurement; the line measurement is beneficially implemented over an extensive area, thereby providing effectively an area measurement. This line measurement ensures that a larger area is monitored using a single sensor, providing a more representative measurement of hydrate formation without increasing measurement complexity. Beneficially, the layout of the sensor for executing a line measurement can be tailored to an extensive area to be sensed, for instance by wrapping it around a volume enclosed by a pipe in a spiral manner. Aforementioned previously proposed techniques using a point open-ended probe are also limited by a characteristic that one mechanical dimension pertaining thereto defines both a sensitivity depth and an operating range with regard to measurement permittivity and frequency. In contradistinction, for the present invention, a sensitivity depth and an operating range can be controlled independently on account of the line measurement providing an extra degree of design freedom. Furthermore, the precision in permittivity measurement provided by way of the line measurement is enhanced for the line sensor in comparison to the previously proposed techniques using an open-ended probe, due to the fact that line measurements are more sensitive and because both transmission and refection measurements can be combined together in a synergistic manner. The functionality of the sensor or sensors can be increased by combining two or more transmission line sensors. In one optional configuration, for example as illustrated in FIG. 3G, such a combination makes it possible to achieve information about both the thickness of deposit layers and the permittivity of the layer. In another optional configuration of the sensor or sensors, there is provided associated apparatus coupled to the sensor or sensors for implementing a switching measurement method for measuring impedance between different sensors, thereby enabling information about bulk properties at low frequencies to be acquired.

Moreover, to ensure that the hydrate growth probability is the same for the area directly in front of the sensor as for the rest of the pipe wall, a thin layer may be attached, or otherwise provided, at the front of the sensor, covering either all of the sensor or a part of the sensor, the layer having the same wettability characteristic (i.e. the same properties with respect to hydrate growth) as the pipe wall; for example, the layer has similar hydrophobic or hydrophilic properties relative to an inside surface of the pipe wall. This layer comprises a material which is beneficially electrically isolating; optionally, the material is added using a sputtering technique. It is to be borne in mind that the complex permittivity includes the dielectric constant, the dielectric losses and the conductivity, and that the measurements include conductivity measurements and dielectric spectroscopy. Such spectroscopy is optionally executed using spot or swept frequency measurements; alternatively, pulse measurements can be employed wherein response signals to pulse excitation are analysed.

Figure 1A:
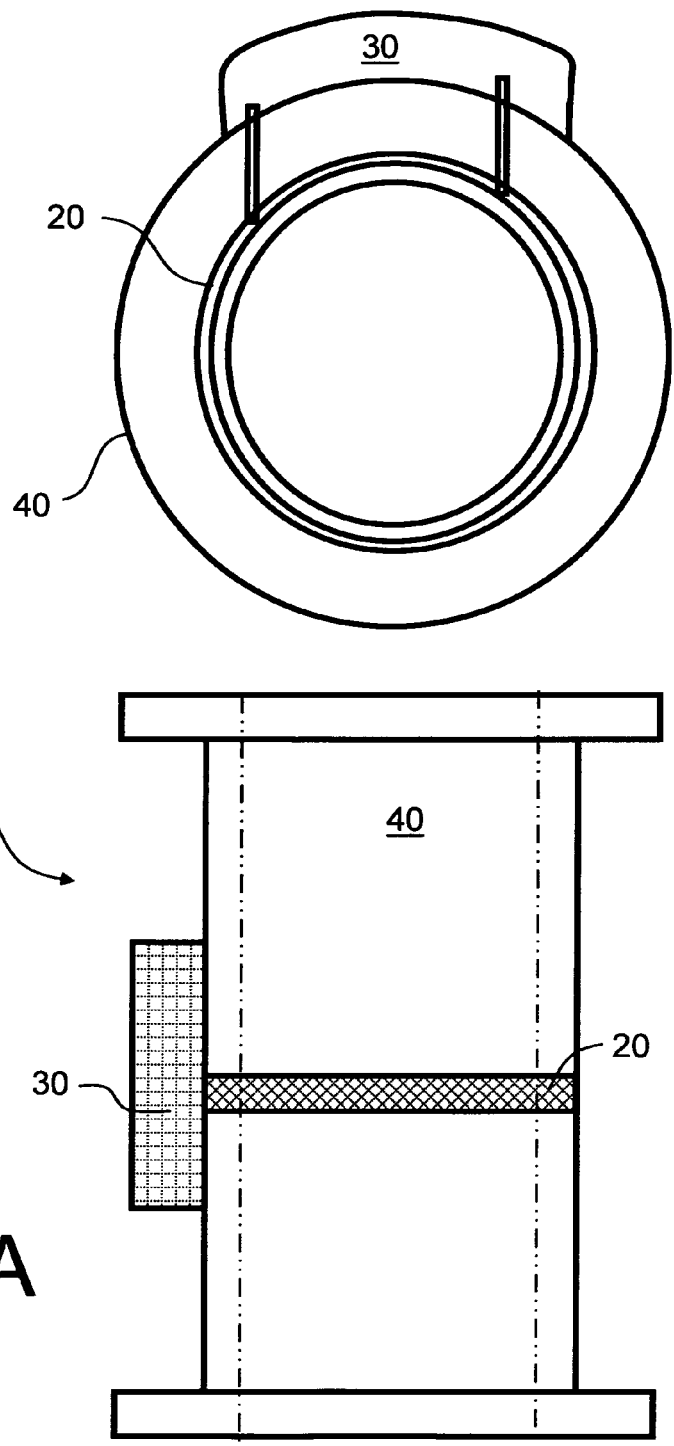
Figure 1B:
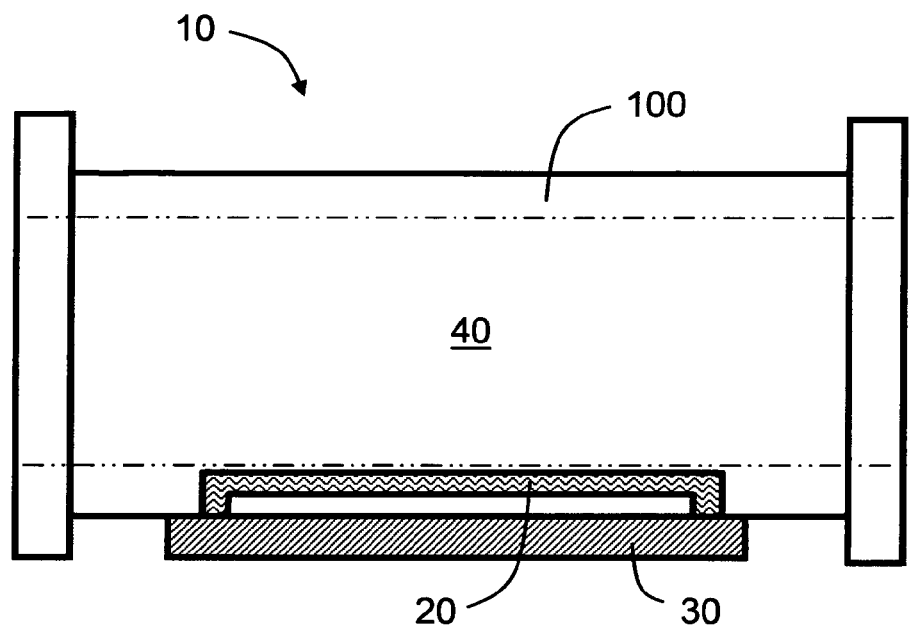
Figure 1C:
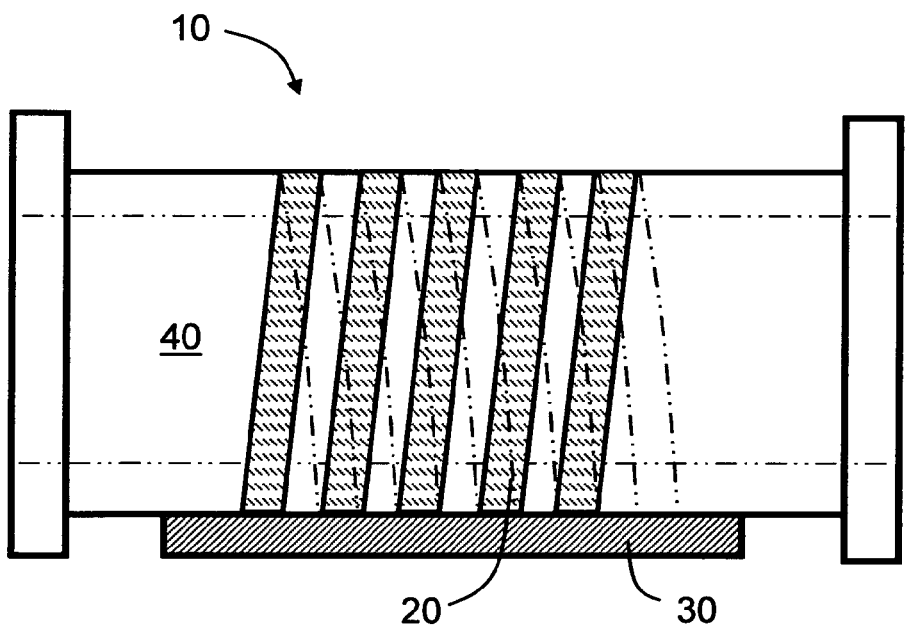

In FIG. 1A, there is shown an inline measuring apparatus for performing permittivity measurements, for example over a range of frequencies in a manner of spectral measurement, optionally implemented using pulse excitation techniques; the instrument is indicated generally by 10. One example installation of the instrument 10, referred to also as being an "apparatus", is in a spool-piece in a pipeline 40 as shown in FIG. 1A. The instrument 10 includes a sensor arrangement 20 disposed in a circumferential manner around a portion of the pipeline 40. An alternative disposition of the sensor arrangement 20 is axially along the pipeline 40 as illustrated in FIG. 1B. A yet alternative disposition of the sensor arrangement 20 is spirally along the pipeline 40. Thus, the sensor arrangement 20 may be placed either in parallel with a central elongate axis of the pipeline 40 or perpendicular to the central elongate axis of the pipeline 40 as illustrated in FIG. 1A and FIG. 1B. Optionally, the sensor arrangement 20 is implemented both parallel in an elongate manner with the pipeline 40, and also perpendicular in an elongate manner with the pipeline 40, for example in a "T"-like implementation. Optionally, as aforementioned, the sensor arrangement 20 is implemented in a spiral manner around a region enclosed by the pipeline 40 as illustrated in FIG. 1C; for example, when the pipeline 40 is fabricated from an insulating dielectric material, for example PEEK or ceramic material, the sensor arrangement 20 is disposed around an outer surface of the pipeline 40; optionally, the sensor arrangement 20 is circumferentially surrounded by exterior screening material and mechanical protection. The sensor arrangement 20 optionally includes a plurality of sensors, for example disposed in a mutually coupled configuration to be interrogated by a common signal applied thereto in operation. Alternatively, the sensor arrangement 20 includes a single spatially extensive sensor, for example implemented as an elongate line sensor, for example an elongate transmission line sensor. Moreover, the sensor arrangement 20 is coupled to an electronics unit 30, namely an electronics apparatus, which generates an electromagnetic signal, and computes a permittivity of a sample volume within the pipeline 40 based upon reflection and/or transmission coefficients and/or impedance associated with a signal received at the sensor arrangement 20 from the fluid within the pipeline 40. A sample volume in which the sensor 20 measures permittivity can be modified by changing geometries and materials used for fabricating the sensor arrangement 20; optionally, the sample volume is dynamically altered by electronically modulating sensing characteristics of the sensor arrangement 20 as will be elucidated later. As aforementioned, the sensor arrangement 20 may include an interfacing layer presented to an interior of the pipeline 40, the layer having a similar wettability in respect of hydrates to a remainder of an inner surface of the pipeline 40.

Figure 4:
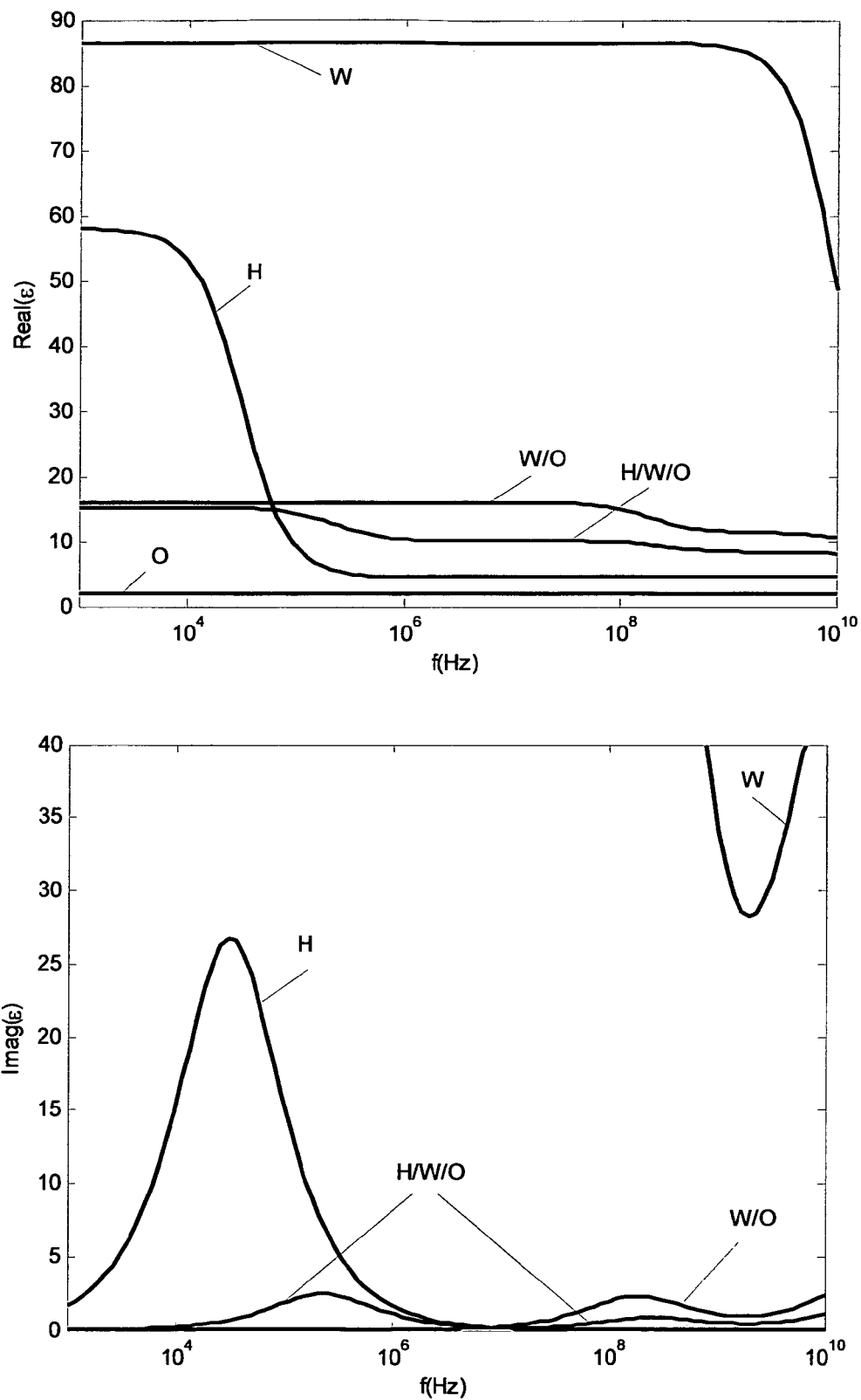
FIG. 4 is a set of graphs showing changes of real (Real($\in$)) and imaginary (Imag($\in$)) components of relative permittivity for separate phases of oil (O), water (W) and hydrate (H), of a water/oil mixture (W/O) and of a hydrate/water/oil mixture (H/W/O) as a function of radiation interrogation frequency (f)

The instrument 10 employs, as a basis for its operation, a characteristic that the complex permittivity spectra are significantly different for the different fluids which may be part of the multiphase fluid present within the pipeline 40 when in use. As an example, the real (Real($\in$)) and imaginary (Imag ($\in$)) parts of the relative permittivity of conductive water (W), oil (O), hydrate (H), a water/oil mixture (W/O) and a hydrate/water/oil mixture (H/W/O) as a function of frequency (f) are shown in FIG. 4. It is observed that there are significant differences in the complex permittivities of the fluids in question. In particular, there are frequency dependencies in the permittivity of hydrate which are exploited in the instrument 10 in order to distinguish variations in permittivity due to hydrate formation from variations in permittivity due to other causes, for example inhibitors, temperature/pressure changes and so forth. In FIG. 4. it is to be observed how this frequency dependency in the permittivity of hydrate influences the permittivity of a water/oil mixture by comparing the permittivity spectrum of the water/oil mixture with the corresponding spectrum for the water/oil/hydrate mixture. Thus, when the amount of hydrate changes in the measurement volume within the sensitivity range of the sensor arrangement 20, the permittivity is correspondingly changed. Based on the measured permittivity in a plurality of frequencies, it is thus possible to calculate the hydrate fraction in the measurement volume.

Figure 2:
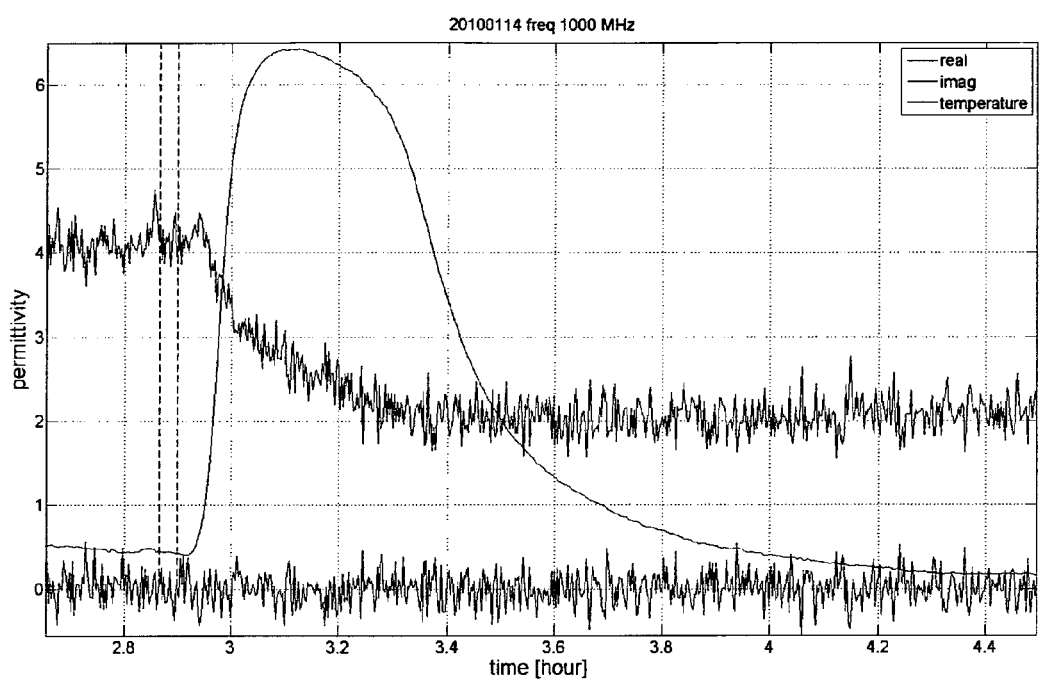
FIG. 2 is an illustration of a dielectric response characteristic during measurement by the instrument of FIG. 1A and FIG. 1B during hydrate formation.

An example of a measurement of the change in measured permittivity during hydrate generation for a single frequency is shown in a graph of FIG. 2. The graph includes an abscissa axis denoting passing of time in hours from left to right, and an ordinate axis denoting a measure of relative permittivity increasing from bottom to top in the graph. A significant variation in permittivity is observed when the hydrate fraction within the measurement volume starts to increase around 3 hours into measurements presented in FIG. 2; the hydrate formation occurs from a mixture of cyclopentane, water and a surfactant (Span 80). The measurements were made for an interrogation signal having a frequency of 1 GHz. Hydrate formation is found potentially to occur very suddenly when conditions allow, for example within a few minutes or less.

The present invention encompasses several different methods of measuring the complex permittivity of fluids present in the pipeline 40. One of these several methods concerns time domain reflectometry (TDR), namely using a time domain approach. TDR is based on measuring a step response or an impulse response of the medium under test included within the pipeline 40. Another method involves using a frequency domain approach in which an oscillator circuit generates a high frequency oscillating signal, which is transmitted to the sensor arrangement 20; the oscillator is beneficially swept or stepped within a frequency range and corresponding permittivity characteristic of the fluids present in the pipeline 40 are computed for each of the swept or stepped frequencies. By data processing the measurements obtained for each of the swept or stepped frequencies, for example by resolving differential sensitivities of a plurality of sensors of the sensors arrangement 20 to different components present in the pipeline 40 close to the inner wall thereof, an analysis of the amounts of the components present using the instrument 10 is thereby feasible.

In addition, for detecting and providing early warning of hydrate deposits, the instrument 10 is susceptible to being used in several other technical applications:

(i) for detecting formation water, for example a break-through of formation water; when formation water is produced, the water fraction and the salinity of the water in the fluid film close to a wall of the pipeline 40 will be increased; the instrument 10 is capable of performing such measurements;

(ii) for detecting and providing early warning regarding the formation of deposits of wax and/or scale on the wall of the pipeline 40; such scale can, for example, include sulphate and carbonate materials; such scale and/or wax deposits can be measured in similar fashion to hydrate deposits; and (iii) for measuring a water content in a fluid film forming along the wall of the pipeline 40.

The electronics unit 30 is beneficially adjusted to be able to measure the amount of formation water in a liquid film formed onto an inside wall of the pipeline 40.

Methods of determining the conductivity and salinity of water-continuous mixtures are already known, but there is a need for more accurate measurement methods for detecting conductivity and salinity of oil-continuous mixtures, for example in order to identify break-through of formation water as early as possible. In the following description, an algorithm for measuring the salinity of water in an oil-continuous flow is presented.

The effective permittivity of a water-in-oil emulsion mixture ($\in^*$) can be calculated using the Hanai-Boyle-Bruggemans model of an emulsion as defined by Equation 1 (Eq. 1);

$$\frac{(\varepsilon^* - \varepsilon_2^*)}{(\varepsilon_1^* - \varepsilon_2^*)}\left(\frac{\varepsilon_1^*}{\varepsilon^*}\right)^{1/3} = 1 - \phi \quad \text{Eq. 1}$$

wherein
$\phi$=the volume fraction of the dispersed phase (water);
$\in_1^*$=the permittivity of the continuous phase (oil); and
$\in_2^*$=the permittivity of the dispersed phase (water).

The conductivity of the water drops is related to the water permittivity as defined in Equation 2 (Eq. 2):

$$\varepsilon = \varepsilon' - j\varepsilon'' - j\frac{\sigma}{\varepsilon_0 \omega} \quad \text{Eq. 2}$$

wherein
$\omega$=the angular frequency ($2\pi$ frequency);
$\in_0$=the permittivity of free space.

Referring to FIG. 4, there is shown graphs of a typical dielectric spectrum of a water-in-oil emulsion (W/O). A change of response as a function of frequency in frequency observed in a frequency range around approximately 100 MHz is due to the conductivity of the water drops, and is referred to as the Maxwell-Wagner-Sillars effect. The frequency where the dielectric loss has its maximum is referred to as the dispersion frequency and is theoretically given by Equation 3 (Eq. 3):

$$f_d = \frac{1}{2\pi\varepsilon_0} \frac{(1-\phi)\sigma_2}{3\varepsilon_1 + (1-\phi)(\varepsilon_2 - \varepsilon_1)} \quad \text{Eq. 3}$$

This Equation 3 (Eq. 3) is only valid for low concentrations of water, and it is therefore beneficial to estimate the dispersion frequency by solving Hanai-Boyle-Bruggeman's equation iteratively.

In FIG. 7, there is shown the dispersion frequency as a function of conductivity for a water-in-oil emulsion with a 10% water concentration calculated using Equation 3 (Eq. 3).

The water fraction is found from the mixture permittivity using the aforesaid Hanai-Boyle-Bruggemans model, and the water conductivity can then be derived from the dispersion frequency. The salinity of the water can then be calculated using known relationships. A sudden increase in the salinity and/or water fraction indicates a break-through of formation water and thereby an increased risk for hydrate formation The instrument 10 is capable of being implemented with its associated sensor arrangement 20 in several different embodiments which will now be described with reference to FIG. 3A to FIG. 3H.

Figure 3A:
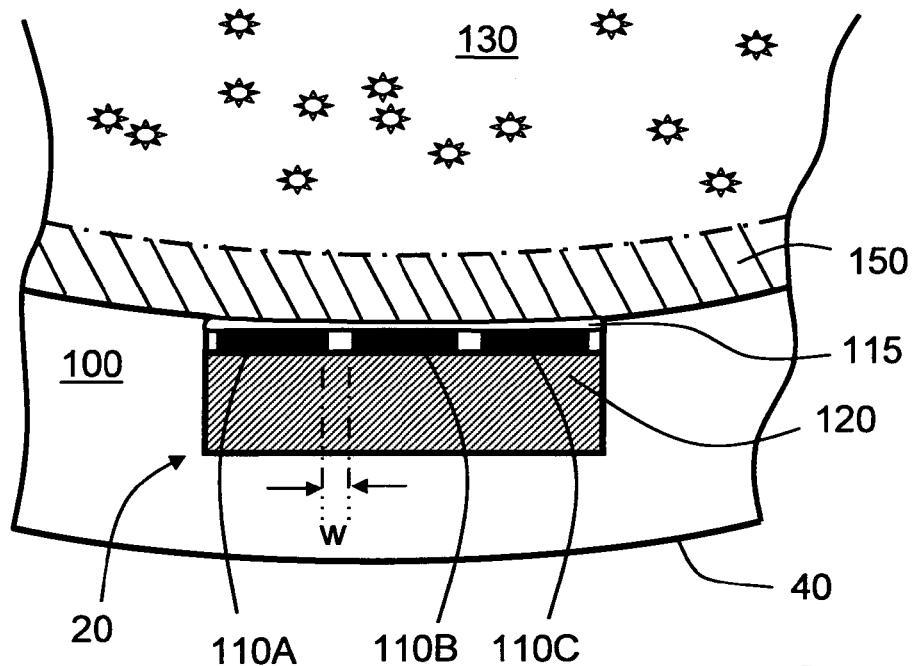
FIG. 3A to FIG. 3H are examples of implementations of a sensor arrangement of the instrument of FIG. 1A and FIG. 1B.

In FIG. 3A, there is illustrated the sensor arrangement 20 implemented as a co-planar waveguide sensor incorporated into a recess in a wall 100 of a pipeline 40. The sensor arrangement 20 is illustrated disposed axially along the wall 100, namely in a manner depicted in FIG. 1B. Optionally, the sensor arrangement 20 is implemented in a circumferential manner a depicted in FIG. 1A. In FIG. 3A, the sensor arrangement 20 includes a configuration of electrodes 110A, 110B, 110C backed by a dielectric material mount 120. An interface layer 115 is optionally included between the electrodes 110A, 110B, 110C and an interior region of the pipeline 40. The electrodes 110A, 110C are beneficially grounded/Earthed and the electrode 110B is actively driven during measurements performed by the instrument 10. The electrodes 110A, 110B, 110C couple efficiently to a film 150 potentially forming onto an inside surface of the pipeline 40; the film 150 is, for example, a collection of hydrate particles forming on account of conditions suitable for hydrate formation pertaining within the pipeline 40. The pipeline 40 conveys, for example, in operation a gas 130 as illustrated. The electrodes 110A, 110B, 110C in combination with their dielectric material mount form a co-planar waveguide which is strongly coupled locally to the film 150 when present. Moreover, the electrodes 110A, 110B, 110C can be formed as longitudinal and/or circumferential strips, otherwise as discrete electrode islands. The electrodes 110A, 110B, 110C are beneficially coupled to the electronics unit 30. Although the electronics unit 30 is shown in FIG. 1A, FIG. 1B and FIG. 1C attached to a side of the pipeline 40, it will be appreciated that the electronics unit 30 can be mounted remotely from the pipeline 40 if required, for example due to a potential high temperature of operation of the pipeline 40.

Figure 3B:
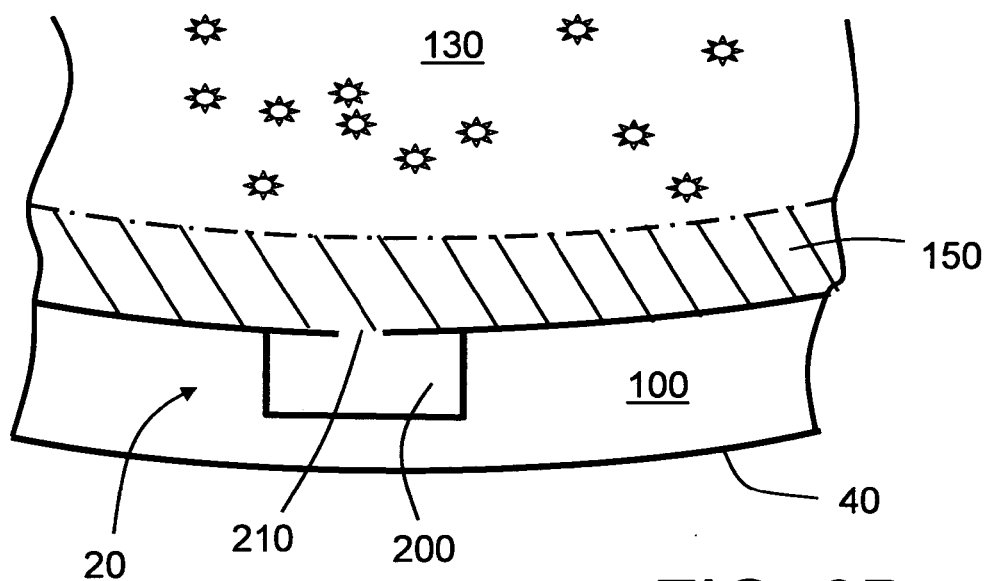

Referring to FIG. 3B, the sensor arrangement 20 is implemented as a hollow or filled waveguide 200 formed into the wall 100 of the pipeline 40 as illustrated. FIG. 3B is a cross-section view across a section of the pipeline 40, namely a configuration as illustrated in FIG. 1B. Microwave energy propagating in the waveguide 200 is coupled to the film 150 via a small aperture 210 provided on an inside surface of the wall 100; beneficially, the small aperture 210 renders the waveguide 200 to be a leaky waveguide which is weakly coupled to an interior region of the pipeline 40. The waveguide 200 can optionally be implemented as an elongate axial or circumferential or helical structure, or alternatively implemented as an interlinked series of microwave waveguide chambers, for example for providing complete area coverage. The waveguide 200 is coupled to the electronics unit 30. Optionally, the aperture 210 can be provided with a window having similar wettability to a remainder of an inwardly facing surface of the pipeline 40. Optionally, the waveguide 200 can be implemented with an inner conductor, such that it operates as aforementioned as a leaky coaxial cable.

Figure 3C:
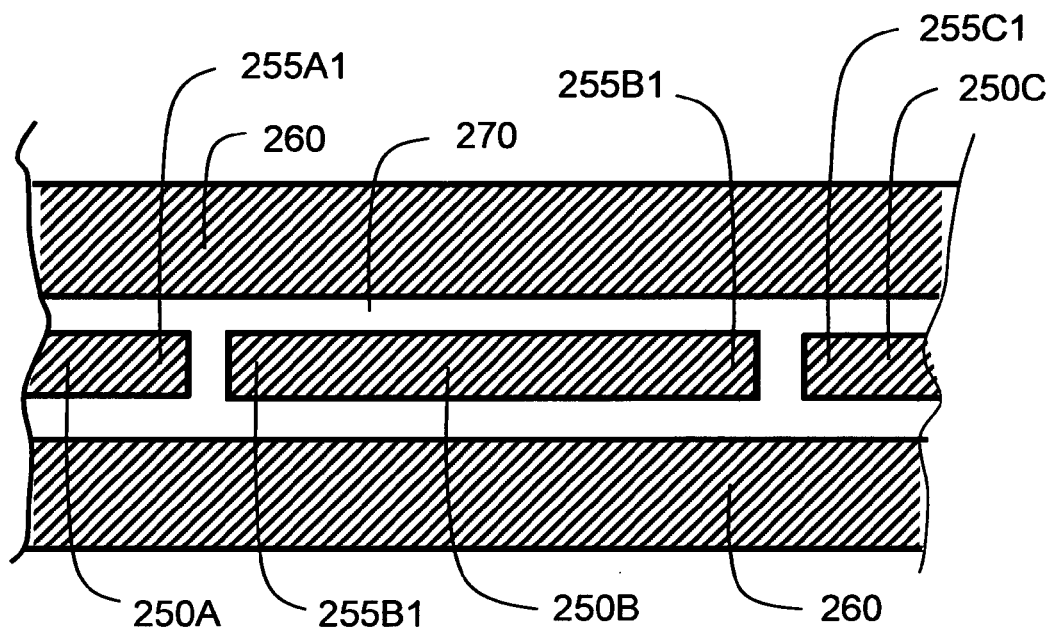

Referring to FIG. 3C, an implementation of the sensor arrangement 20 is shown in plan view looking from a centre of the pipeline 40 towards the wall 100. The sensor arrangement 20 includes a co-planar waveguide resonator 250, for example denoted by 250A, 250B, 250C, surrounded by ground or shielding electrodes 260 separated by a region of substrate dielectric 270. The resonator 250, namely functioning as a transmission line, is operable to guide microwave energy therealong which couples into the film 150 formed onto an inside surface of the wall 100. The sensor arrangement 20 of FIG. 3C is disposed circumferentially, spirally and/or axially around the pipeline 40. Moreover, the resonator 250 functioning as a transmission line is beneficially insulated from the ground or shielding electrodes 260 by way of a dielectric material region 270 exhibiting low loss at microwave frequencies, for example by using a ceramic or polymer plastics material in the region 270. The transmission line resonator 250 is coupled to the electronics unit 30. Each transmission line resonator 250 is an elongate conductor having a first end, for example an end 255B1 of a resonator 250B, and a second end, for example an end 255B1 of the resonator 250B. The transmission lines 250A, 250B, 250C couple interrogating radiation at their ends by capacitive and/or radiative coupling. Optionally, the sensor arrangement 20 of FIG. 3C is passivated in a thin layer of a dielectric material having a similar wettability to an inwardly facing surface of the wall 100 of the pipeline 40.

Figure 3D:
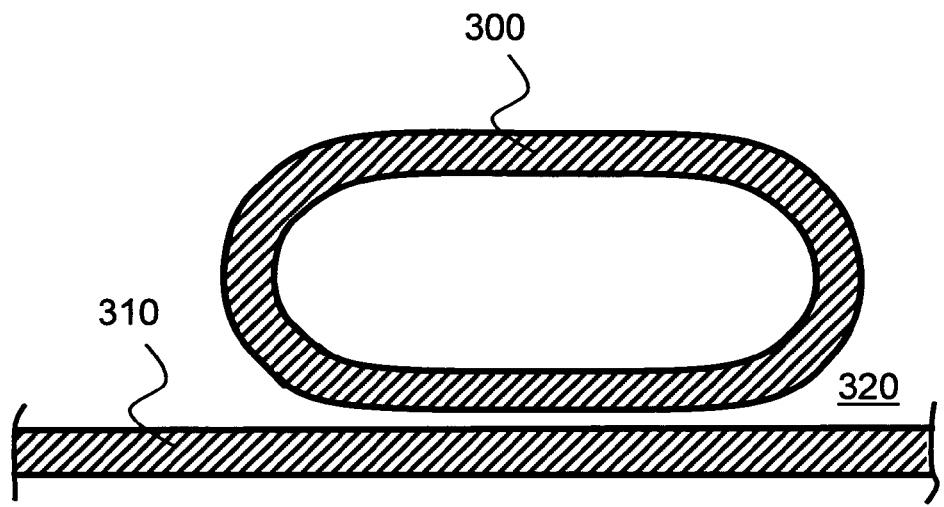

Referring to FIG. 3D, the sensor arrangement 20 is implemented as a microstrip resonator 300 disposed in close proximity to a feed transmission line 310. FIG. 3D is a plan view from a central axis of the pipeline 40 looking towards an inwardly facing surface of the wall 100. Microwave signals from the electronics unit 30 are capable of propagating along the feed transmission line 310 and coupling into the resonator 300 housed within the wall 100 of the pipeline 40 and thereby coupling efficiently into the film 150. The resonator 300 includes an inner hollow volume as illustrated. Optionally, the resonator 300 is mechanically supported on an intervening dielectric material 320, for example a ceramic material or a plastics polymer material. The resonator 300 is beneficially disposed in an axial row and/or a circumferential row and/or a helical row in the wall 100 of the pipeline 40.

Figure 3E:
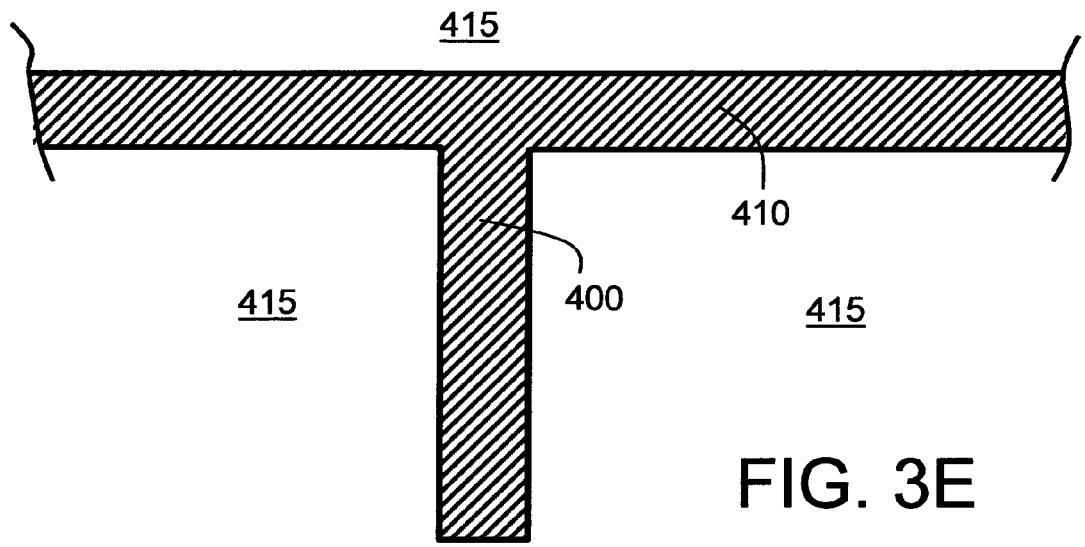
Figure 3F:
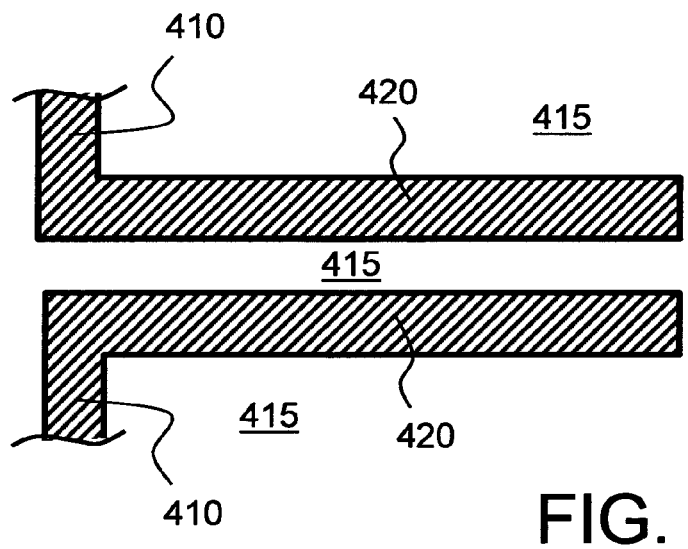
Figure 3G:
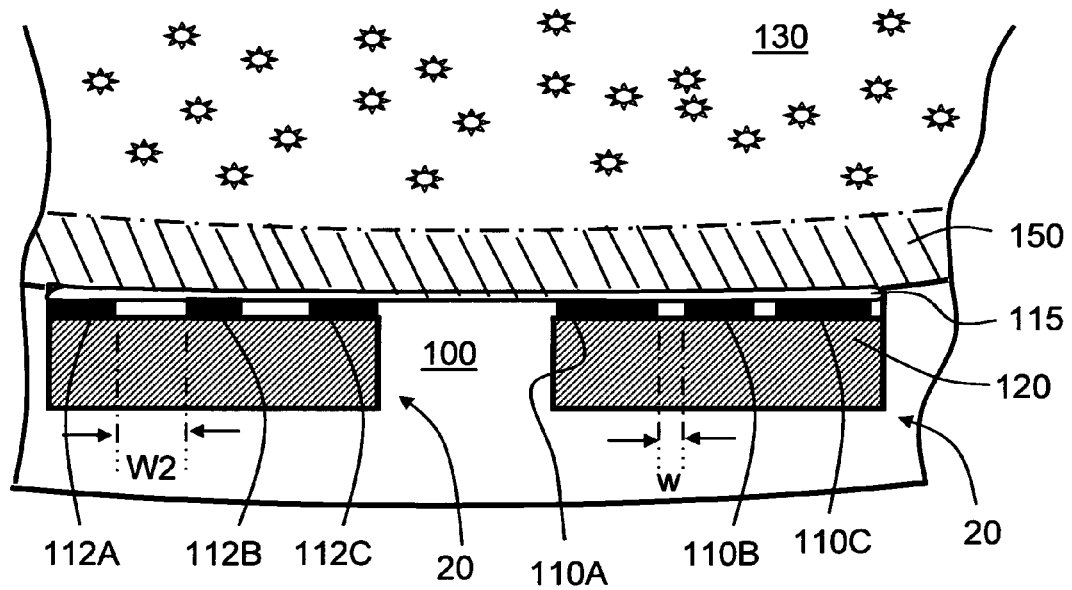

Referring to FIG. 3E, the sensor arrangement 20 is implemented as one or more stub resonators 400 fed from a feed transmission line 410 coupled to the electronics unit 30. FIG. 3E is a plan view seen from a central axis of the pipeline 40 looking towards an inwardly facing surface of the wall 100. The one or more stub resonators 400 are operable to couple into the aforementioned film 150 potentially formed in operation onto an inwardly facing surface of the wall 100 of the pipeline 40. The one or more stub resonators 400 are beneficially disposed in an axial and/or circumferential and/or helical (spiral) manner in one or more recesses machined into the inside surface of the pipeline 40. In FIG. 3F, there is provided an illustration of a further implementation of the sensor arrangement 20 as a dipole resonator 420 with open or shorted ends; the dipole resonator 420 is also known as a parallel coupled microstrip resonator. One or more of the dipole resonators 420 are beneficially coupled to the electronics unit 30 and are disposed in an axial, circumferential and/or spiral (helical) arrangement within the wall 100 of the pipeline 40. The one or more stub resonators 400 and their associated feed transmission line 410 are beneficially formed on a dielectric substrate 415. Moreover, the resonators 420 are beneficially covered in a thin interfacing layer (not shown) facing into an interior region of the pipeline 40, the thin interfacing layer having similar wettability characteristics in comparison to an inside-facing surface of the wall 100 of the pipeline 40; hydrate, wax, break-through of formation water and/or scale deposition onto the thin layer is thus representative of similar deposit onto the wall 100. For the sensor arrangement 20 shown in FIG. 3A to 3F, the thin layer interfacing facing to an interior of the pipeline 40 beneficially has a thickness in a range of 20 µm to 2 mm.

Figure 3H:
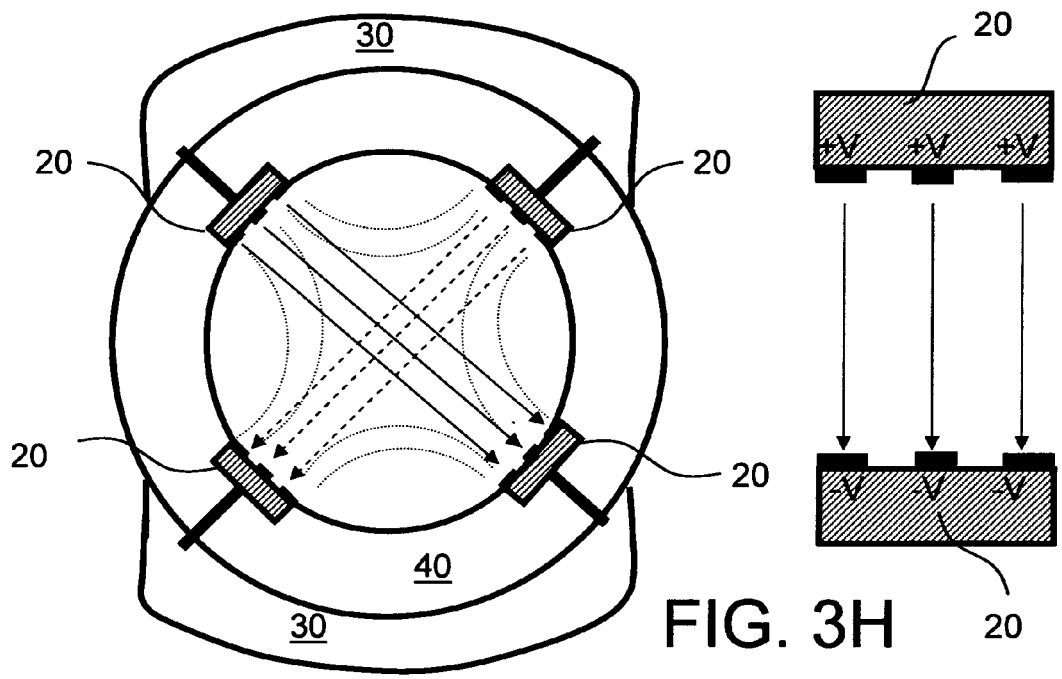

Referring to FIG. 3G, there is shown a sensor arrangement which includes two sensors, wherein each sensor corresponds to the sensor shown in FIG. 3A, wherein the two sensors in FIG. 3G are provided with mutually different gaps between their respective electrodes, namely imparting them with mutually different sensing characteristics. Thus, the two sensors in FIG. 3G have mutually different sensitivity depths and are thereby capable of being employed to measure both the thickness of the deposit layer 150 and the permittivity of the layer 150 formed on an inside surface of the pipeline 40. Furthermore, low frequency impedance measurements between electrodes in different sensors, for example a gap w between electrodes 110, 112, in addition to the aforementioned transmission/reflection measurements renders it possible to calculate the permittivity at lower measurement frequencies. For this purpose, capacitive measurements are beneficially applied in oil-continuous mixtures, whereas resistive/conductive measurements are beneficially applied in water-continuous mixtures. The sensitivity depth of these measurements can be controlled by changing the effective distance w between electrodes of the sensors in FIG. 3G, for example by mechanical or by electronically resolving between an electrode arrangement including a plurality of mutually clustered electrodes. As illustrated in FIG. 3H, the sensor arrangement 20 is beneficially implemented so that bulk measurements of the low frequency permittivity and/or conductivity are beneficially implemented by placing the sensors on mutually opposite sides of the pipeline 40. Beneficially, an electronic measurement device is included for switching in operation between transmission/reflection coefficient measurements, and impedance measurements, for example capacitance and/or resistance measurements, are beneficially employed in this configuration of FIG. 3H. For measurements between two sensors, all or some of the electrodes on one sensor are operably set at a high potential, while all or some of the electrodes on the other sensor are set at a low potential. The low frequency permittivity is determined by measuring the capacitance between the sensors, namely by performing an a.c. measurement, whereas the conductivity is found by measuring the resistance between the sensors. This can be optionally done by performing a substantially d.c. measurement, or optionally by an a.c. measurement.

Referring next to FIG. 1C, a combined transmission line and inductive sensor implementation of the sensor arrangement 20 is beneficially a coplanar waveguide, for example as shown in FIG. 3A. The transmission line sensor operates as described earlier, whereas the inductive implementation can be configured by applying the same signal voltage to all three electrodes 110A, 110B and 110C, such that electrodes function in a manner of a magnetic solenoid for conducting inductive interrogating currents generated by the electronics unit 30. By employing this configuration, both the near wall permittivity and the bulk permeability can be measured in a synergistic manner. The inductive implementation can also be used to measure eddy-current losses in a flow of fluid through the pipeline 40, wherein the eddy-current losses can be correlated to water content measurements as described in various patents and patent applications. Such an approach is especially beneficial for coping with measurement of multiphase fluid within the pipeline 40 and associated deposited films 150. Operation of an inductive solenoid to measure permeability characteristics is described in a published patent application no. WO 01/07874 A1 (PCT/NO00/00236; Erling Hammer; "Methods and Devices for Measuring Interface Levels between Fluids, and Uses thereof") which is hereby incorporated by reference. In other words, the electrodes 110A, 110B, 110C are configured by the electronics unit 30 in a first mode to function to measure permittivity and localized spatial extent of the deposition layer 150 by operating as a high-frequency transmission line, and in a second modes to function as a magnetic solenoid to measure bulk permeability and/or permittivity characteristic over an entire cross-section of an interior of the pipeline 40. Such operation enables the instrument 10 to provide a high degree of synergistic functionality and obtain potentially a large volume of data representative of conditions within the pipeline 40.

Thus, in one preferred embodiment of the invention, the sensor arrangement 20 is implemented to include a coplanar waveguide as shown in FIG. 3A. In another embodiment of the invention, the sensor arrangement 20 is implemented to include a leaky waveguide as shown in FIG. 3B. Alternatively, the sensor arrangement 20 is implemented to employ various forms of microwave resonators as illustrated in FIG. 3C to FIG. 3F. Measurables derived from the sensor arrangement 20 may be either the reflection coefficient, the transmission coefficient or both. As aforementioned, a preferred embodiment is to employ a coplanar waveguide and to execute in operation a combination of impedance, reflection and transmission measurements. At low frequencies, for example in a range of kHz, the impedance between two sensors is preferable measured, whereas reflection and transmission measurements are preferable executed in operation at higher frequencies, for example in a range of MHz and/or GHz. For a given sensor geometry, reflection measurements are preferable for measuring materials with high permittivities, for example mixtures having a high water content; for measurements in the lower frequency operating range, transmission measurements are preferable for materials with low permittivity, for example mixtures with low water content, for example less than 25%, and for measurements in the higher frequency operating range. In contrast, a combined reflection/transmission measurement is preferable for materials with intermediate permittivity and for measurement in an intermediate frequency operating range, for example in a frequency range of 100 MHz to 1 GHz. Thus, pursuant to the present invention, a combination of reflection and transmission measurements gives a largest operating range with regard to frequency and permittivity. The measurements are generally made for a plurality of frequencies or for a frequency band, but may in some embodiments also be made for only a single frequency or a narrow frequency range. By "narrow frequency range", a frequency variation of less than +/−5% about a mean frequency is optionally utilized, more preferable less than +/−1%. Yet alternatively, temporal pulse techniques are employed for determining the reflection coefficient, the transmission coefficient or both. In another implementation of the instrument 10, resonator methods are used to calculate the dielectric constant and dielectric losses for a single frequency or a plurality of frequencies with higher accuracy. In this case the dielectric constant and the dielectric losses are calculated based on measured resonance frequency and Q-factor. Such resonance measurement are susceptible to increase measurement sensitivity and/or measurement signal-to-noise ratio.

The sensor arrangement 20 sensitivity range is scalable by changing some of the design parameters for the sensor arrangement 20. For an example embodiment of a coplanar waveguide sensor employed for implementing the sensor arrangement 20, the sensor sensitivity range can be scaled by changing a spacing between the conductors and/or exchanging the substrate material to a material with a different permittivity. An example coplanar waveguide sensor has:
(i) a substrate height in a range of 30 mm to 70 mm, for example substantially 50 mm;
(ii) a transverse electrode width in a range of 1 mm to 4 mm, for example substantially 2 mm;
(iii) a gap width w of in a range of 0.5 mm to 3 mm, for example substantially 1 mm; and
(iv) a substrate relative permittivity in a range of 1.5 to 5, for example substantially 2.1.

Figure 6:
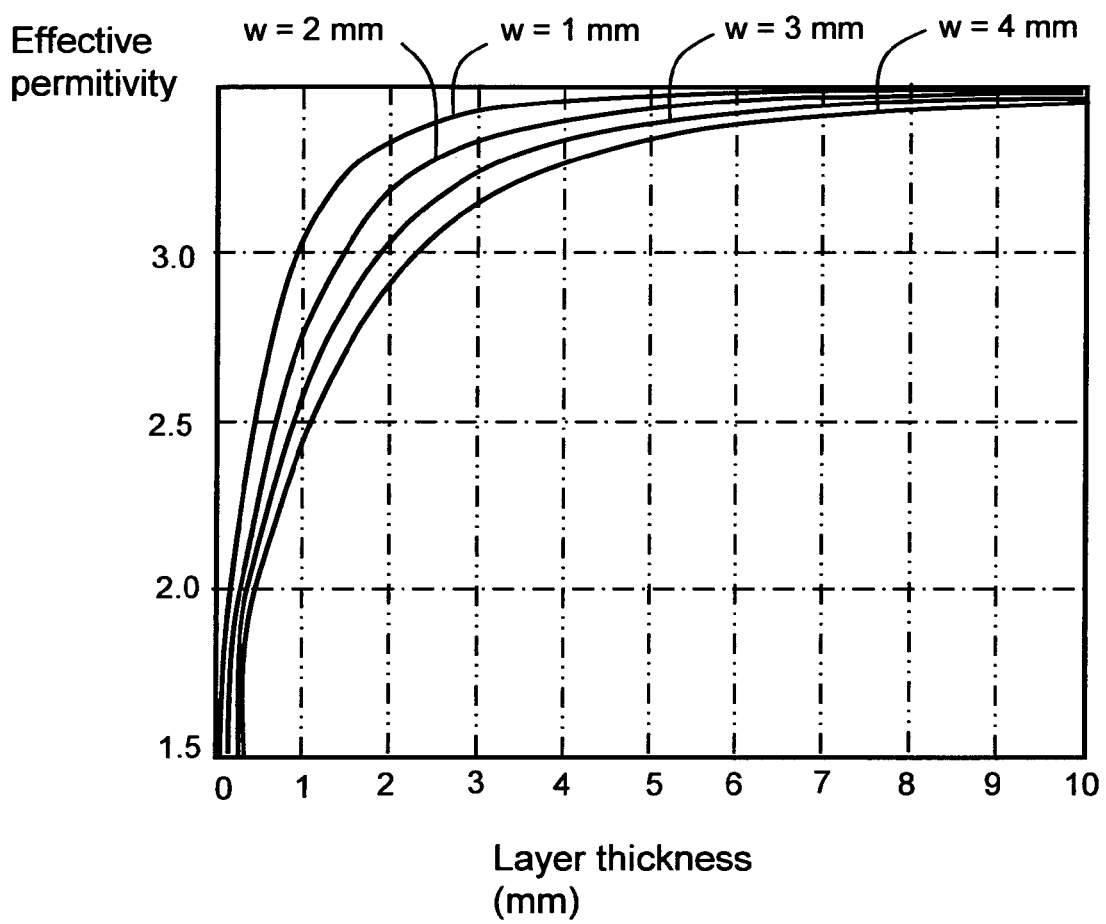
FIG. 6 is a graph of effective relative permittivity of a co-planar waveguide terminated by a hydrate layer backed by gas; there are several curves illustrating an effect on measurement of changing a spacing width w of the waveguide.

As an example of scaling of the sensitivity range, the effect on the sensitivity range of this coplanar waveguide sensor by changing the gap width w between the conductors in FIG. 3A as illustrated in FIG. 6 is pertinent to the present invention. Increasing the gap width w decreases the effective permittivity measured, giving effectively a change in sensitivity range. Note that a transformer section of coplanar waveguide is necessary to couple from a 50 Ohm system to the coplanar waveguide sensor. For an example case of a leaky waveguide, for example as illustrated in FIG. 3B, the sensitivity range can be modified by changing the aperture size. Similarly, there are other design parameters which can be changed for the other configurations. In order to increase the accuracy in the measurements and correct for temperature variations, a reference sensor covered with a medium with known permittivity and thickness larger than the sensors sensitivity range can be used as a component part of the sensor arrangement 20. The reference sensor can be employed, for example, to compensate for systematic offsets as a function of temperature of operation.

Furthermore, to determine accurately the film thickness of a deposit layer 150, a configuration consisting of two or more sensors with different sensitivity ranges can be used, for example a combination of sensors of types as illustrated in FIG. 1 to FIG. 3H. For the case with two sensors, and where the thickness of the deposit layer 150 is smaller than the sensitivity depth of the sensor 20 with largest sensitivity depth, the layer thickness may be determined using a set of two simultaneous equations with two unknown parameters. These simultaneous equations can be solved in the electronics unit 30 on computing hardware therein operable to execute one or more software products recorded on machine readable data storage media.

The thin deposited layer 150 may in some cases consist of only hydrate as discussed above. In other cases, the deposit layer 150 consists of a mixture of hydrate, water and hydrocarbons. In addition, the multiphase flow behind the deposited layer 150 as seen from the sensor arrangement 20, may also contain hydrate in addition to water, hydrocarbons and other fluids that can be present in a multiphase flow through the pipeline 40. The multiple-sensor configuration including two or more different types of sensors for implementing the sensor arrangement 20 with different sensitivity ranges utilized is applicable also for this case, making it possible to determine a hydrate fraction in the thin deposited layer 150 in addition to calculating the thickness of the deposited layer 150. Differentiation between hydrate present in the deposited layer 150 and hydrate present in a fluid flow through the pipeline 40 is computed in the electronics unit 30 by receiving measurement signals from a plurality of sensors of the sensor arrangement 20 exhibiting mutually different spatial sensing characteristics and mutually different sensitivities to components present within the pipeline 40, and then by performing a matrix manipulation, corresponding to solving a plurality of simultaneous equations, to determine amounts and spatial extent of different components present in the deposited layer 150 as well as optionally a composition of material present in fluid flow through the pipeline 40.

Figure 5:
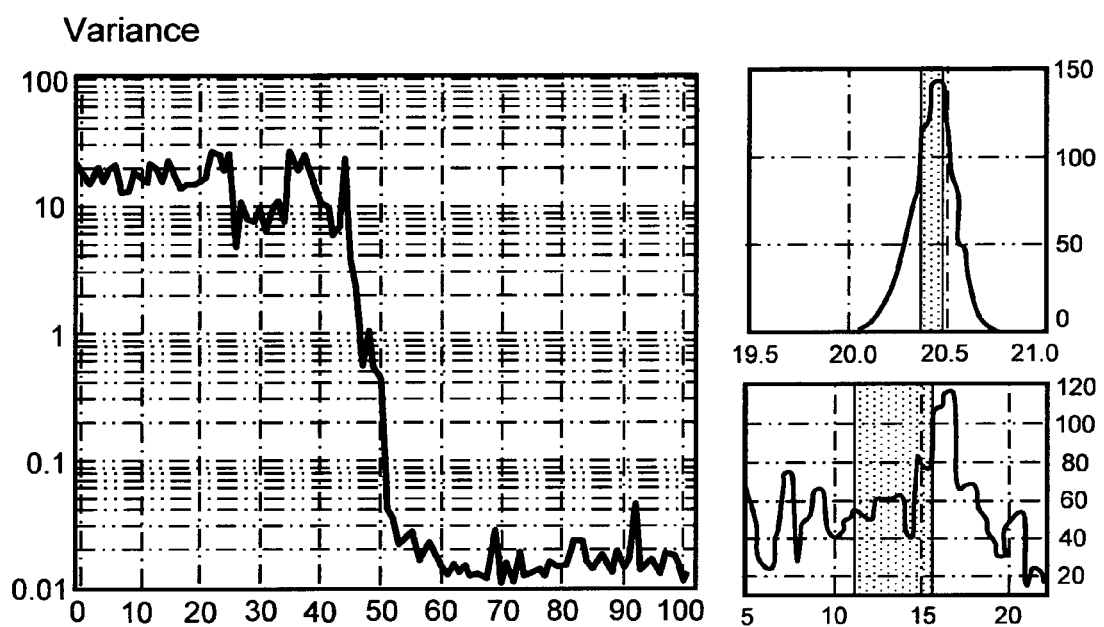
FIG. 5 is a graph of a variance in reflected time signal as a function of time for executing a measurement of hydrate layer thickness.

It is also possible to determine the thickness of a deposit layer 150 using a single sensor for implementing the sensor arrangement 20 pursuant to the present invention. In this case, variations of the time signal is studied, see FIG. 5, and these variations are investigated statistically. The measured permittivity when an oil-water-gas is flowing in the pipeline 40 will show fluctuations with time as the fluid passing the sensor arrangement 20 will not be homogeneous. The sensitivity of the sensor arrangement 20 described in this invention decreases exponentially with the distance from the pipeline wall 100. If a hydrate layer 150 is deposited on the pipeline wall 100, the measured permittivity fluctuations will decrease. Thus, the measured variation in the permittivity $\in$ is a function of a thickness of the layer 150, and a reduction in permittivity fluctuation is an early warning that a hydrate layer 150 is building up. In FIG. 5, a screenshot from a computer program for measurement of hydrate deposit layers using this method is shown. Time series with 1601 measurement points are measured over a time period of 0.8 seconds, and these time series are analyzed statistically using histograms and a variance as a function of time is computed. This method is beneficially used for determining a hydrate fraction in the measurement volume of the sensor arrangement 20. When the hydrate fraction in the measurement volume is increased, the variance decreases. It has been observed that the variance may change with a factor of 1000 and the kurtosis may change with a factor of 100 000. Thus, the present invention provides a very considerable improvement to known apparatus and associated measurement methods. Optionally, such temporal analysis is combined with aforementioned solving of a plurality of simultaneous equations for obtained a further improved quality of measurement.

The apparatus 10 described in the foregoing beneficially includes a temperature sensor coupled to the electronics unit 30 for measuring a temperature of the sensing region of the sensors arrangement 20; the temperature measurement is beneficially used for increasing an accuracy of measurement of the instrument 10 when predicting formation of a layer on the sensor arrangement 20. Optionally, the electronics unit 30 is also provided with a signal indicative of a pressure within the pipeline 40 in a vicinity of the sensor arrangement 20. The electronics unit 30 is beneficially provided with signals from other types of sensors utilizing different sensing principles, for example:

(i) a capacitive and/or inductive principle, for example a bulk measurement of permittivity of contents of the pipeline 40; and/or (ii) an acoustic principle, for example for performing bulk acoustic measurement of contents within the pipeline 40; optionally, the acoustic measurements are implemented at ultrasonic frequencies, namely in a frequency range of 10 kHz to 1 MHz, and more optionally in a range of 20 kHz to 200 kHz, although other frequency ranges can be employed if desired; and/or (iii) an optical principle, for example for performing bulk optical measurement of contents within the pipeline 40.

Referring next to FIG. 8, there is illustrated an implementation of the sensor arrangement 20 for use with instrument 10 pursuant to the present invention, wherein the dielectric material mount 120 to the elongate transmission line electrodes 110A, 110B, 110C is fabricated from a material whose relative permittivity can be dynamically varied in operation by applying a static electric and/or magnetic field to the material mount 120. The static magnetic field is beneficially generated using a magnetic coil 500 which is driven by a controlled energizing current therethrough for dynamically modulating operation of the sensor arrangement 20, namely for controlling a degree of spatial penetration of an interrogating electric field 510 generated by the electrodes 110A, 110B, 110C into an interior region of the pipeline 40. Additionally, or alternatively, the static electric field is beneficially generated using an electrode arrangement, for example the electrodes 520A, 520B disposed at lateral sides of the material mount 120 as illustrated, namely for dynamically modulating operation of the sensor arrangement 20, namely for controlling a degree of spatial penetration of the interrogating electric field 510 generated by the electrodes 110A, 110B, 110C into the interior region of the pipeline 40. Such spatial control of the electric field 510 enables a nature and spatial extent of thin films formed onto the interior wall of the pipeline 40 to be precisely and reliably characterized using a very simple form for the sensor arrangement 20.

The material mount 120 is beneficially fabricated from a material which includes a dipole moment and is susceptible to being highly polarisable for dielectric tuning purposes. For example, the material mount is beneficially fabricated from a ferromagnetic material whose dielectric properties can be tuned; when a permittivity of the material of the material mount 120 is dynamically increased, the sensing electric field 510 between the electrodes 110A, 110B, 110C is formed to a greater extent into the material of the material mount 120, and to a lesser extent into a central region of the pipe 40. Conversely, when the permittivity of the material of the material mount 120 is dynamically decreased, the sensing electric field 150 generated between the electrodes 110A, 110B, 110C is formed to a lesser extent into the material of the material mount 120, and more into a central region of the pipeline 40 in which film deposition onto inside walls of the pipeline 40 can occur. The material employed for the material mount 120 is beneficially a high dipole moment material, for example a ceramic ferrite material, a electrically polarized ceramic material, a polymer material, on any combination thereof.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. An inline measuring apparatus (10) for measuring at least one of hydrate, wax, scale presence, breakthrough of formation water and an amount of formation water (150) on or close to an inside surface of a wall (100) of a pipe (40), where close to is defined as not more than 20 mm, for guiding fluid in operation, characterized in that the apparatus (10) includes an electronics unit (30) coupled to a sensor arrangement (20) intended to be disposed along the pipeline (40) in a spatially extensive manner, where the sensor arrangement (20) includes an elongated transmission line for sensing at least one of the hydrate, wax, formation water and scale (150) using a line measurement; and the electronics unit (30) in cooperation with the sensor arrangement (20) is configured to perform a series of dielectric measurements at a plurality of interrogating frequencies for determining presence and spatial extent of at least one of the hydrate, wax, scale and formation water (150).

2. An inline measurement apparatus (10) as claimed in claim 1, characterized in that the inline measurement apparatus (10) is configured to utilize complex permittivity measurements within a measurement volume spatially close to a wall of a pipe, to detect amounts of formation water in a liquid film close to the wall of the pipe, in a spatial region therefrom of not more than 20 mm, more preferably not more than 5 mm, and most preferably not more than 1 mm.

3. An inline measurement apparatus (10) as claimed in claim 2, characterized in that the inline measurement apparatus (10) is configured to utilize complex permittivity measurements to determine a salinity and a conductivity in the liquid film formed within the spatial measurement region of the sensor arrangement (20).

4. An inline measuring apparatus (10) as claimed in claim 1, characterized in that the sensor arrangement (20) is configured to be disposed in an axial and/or circumferential and/or spiral manner on an inside surface of the wall (100) of the pipe (40).

5. An inline measuring apparatus (10) as claimed in claim 1, characterized in that the sensor arrangement (20) is configured to be disposed in a multisegment path on an inside surface of the wall (100) of the pipe (40).

6. An inline measuring apparatus (10) as claimed in claim 5, characterized in that the multisegment path is configured to be arranged to cover an area of the inside surface giving an effective 2-dimensional coverage.

7. An inline measuring apparatus (10) as claimed in claim 1, characterized in that the transmission line is implemented as a coplanar waveguide, a leaky waveguide, a microstrip line, or a slotline.

8. An inline measuring apparatus (10) as claimed in claim 1, characterized in that the sensor arrangement (20) is configured to be disposed in a spiral manner around a region enclosed by the pipe (40), and the electronics unit (30) is operable also to employ the sensor arrangement to perform a bulk permittivity and/or eddy-current losses and/or permeability measurement of fluid flowing within the pipe (40).

9. An inline measuring apparatus (10) as claimed in claim 1, characterized in that the sensor arrangement (20) includes several sensors having mutually different sensing properties.

10. An inline measuring apparatus (10) as claimed in claim 1, characterized in that the sensor arrangement (20) includes one or more sensors (20) whose spatial measurement region is dynamically controlled in extent by varying a permittivity of a material included in said one or more sensors.

11. An inline measuring apparatus (10) as claimed in claim 1, characterized in that the inline measuring apparatus comprises more than one sensor arrangement (20) being configured to function in a dual mode including a first operating mode and a second operating mode, wherein the first operating mode is employed for performing spatially local measurements along the pipe wall, and the second operating mode is a bulk impedance mode for which an impedance measurement provides bulk permittivity measurements at frequencies in the range of kHz, between at least one pair of sensor arrangements (20) where the individual sensor arrangements (20) are spatially mutually remote.

12. An inline measuring apparatus (10) as claimed in claim 1, characterized in that the inline measuring apparatus comprises more than one sensor arrangement (20) being configured to function in the dual mode including the first operating mode and the second operating mode, wherein the first operating mode is employed for performing spatially local measurements along the pipe wall, and the second operating mode is a local impedance mode for which an impedance measurement gives local permittivity measurements of liquid film and/or deposits at frequencies in the range of kHz, between at least one pair of sensor arrangements (20) where the individual sensor arrangements (20) are spatially closely spaced.

13. An inline measuring apparatus (10) as claimed in claim 11, characterized in that, in the second operating mode, an electronic measurement device is included for switching in operation between transmission/reflection coefficient measurements and impedance measurements, said measurements at least including capacitance and/or resistance measurements.

14. An inline measuring apparatus (10) as claimed in claim 1, characterized in that the electronics unit (30) is configured to perform time domain reflectometry (TDR) for making a permittivity measurement (150).

15. An inline measuring apparatus (10) as claimed in claim 1, characterized in that the electronics unit (30) is configured to perform a swept or stepped measurement at a plurality of frequencies.

16. An inline measuring apparatus (10) as claimed in claim 1, characterized in that measurables of the apparatus (10) are reflection coefficients and/or transmission coefficients and/or impedance or a combination of these for determining presence and spatial extent of the hydrate, wax, break-through of formation water and/or scale (150).

17. An inline measuring apparatus (10) as claimed in claim 1, characterized in that an interrogating output from the electronics unit is terminated in a matched load.

18. An inline measuring apparatus (10) as claimed in claim 1, characterized in that the sensor arrangement (20) includes a 1-port device terminated in a short circuit.

19. An inline measuring apparatus (10) as claimed in claim 1, characterized in that the sensor arrangement (20) includes a 1-port device terminated in an open circuit.

20. An inline measuring apparatus (10) as claimed in claim 1, characterized in that the sensor arrangement (20) includes at least one of: a planar transmission line resonator (250, 300, 400), a leaky waveguide resonator, a dipole transmission line resonator (420), wherein a hydrate, wax and/or scale content in a measurement volume of the sensor arrangement (20) is determined from a measured resonance frequency and/or a resonance Q-factor.

21. An inline measuring apparatus (10) as claimed in any claim 1, characterized in that said sensor arrangement (20) includes at least one sensor which is configured red to function as a reference sensor which has a material with known material properties throughout its measurement range.

22. An inline measuring apparatus (10) as claimed in any claim 1, characterized in that said sensor arrangement (20) includes an interfacing dielectric material in a thin layer at a front of the sensor arrangement, covering either all of the sensor or a part of the sensor, the layer having the same wettability characteristic as the pipe (40) wall (100) so that the hydrate, wax and/or scale (150) forms in a representative manner on the dielectric material (115).

23. An inline measuring apparatus (10) as claimed in claim 22, wherein the dielectric material (115) is a ceramic and/or a polymer plastics material.

24. A method for measuring at least one of hydrate, wax, scale presence, breakthrough of formation water and an amount of formation water (150) on or close to an inside surface of a wall (100) of a pipe (40) for guiding fluid in operation, characterized in that the method includes:
   (a) using an electronics unit (30) of an apparatus (10) coupled to a sensor arrangement (20) intended to be disposed along the pipeline (40) in a spatially extensive manner, where the sensor arrangement (20) includes an elongated transmission line, to interrogate the sensor arrangement (20) for sensing formation of a layer of hydrate, wax, break-through of formation water and/or scale (150) using a line measurement; and
   (b) using the electronics unit (30) operating in cooperation with the sensor arrangement (20) to perform a series of dielectric measurements at a plurality of interrogating frequencies for determining presence and spatial extent of the layer of hydrate, wax, break-through of formation water and/or scale (150).

25. A method as claimed in claim 24, characterized in that the measurements derived from the sensor arrangement (20) are combined with measurements of one or more of the following types: temperature measurement; capacitive or inductive measurements; bulk measurement of the permittivity; acoustic measurement; and optical measurement.

26. A method as claimed in claim 24, including:
   (c) performing the measurements at a plurality of frequencies using the sensor arrangement (20) including a plurality of sensors exhibiting mutually different spatial measurement characteristics in relation to the layer of hydrate, wax, break-through of formation water and/or scale (150) to create a matrix of measurement values; and
   (d) solving a series of simultaneous equations in the electronics unit (30) using the values in the matrix to determine presence and/or extent of the layer of hydrate, wax and/or scale (150).

27. A method as claimed in claim 26, wherein the mutually different spatial measurement characteristics are implemented by employing mutually different gaps between respective electrodes of the sensor arrangement (20).

* * * * *